United States Patent [19]

Vandenbooren et al.

[11] 4,158,095
[45] Jun. 12, 1979

[54] PROCESS FOR THE PREPARATION OF 5-(4-AMINO BUTYL)-HYDANTOIN AND/OR 2-UREIDO-6-AMINO-HEXANOIC ACID AMIDE

[75] Inventors: Franciscus H. A. M. J. Vandenbooren; Egidius J. M. Verheijen, both of Geleen, Netherlands

[73] Assignee: Stamicarbon, B.V., Geleen, Netherlands

[21] Appl. No.: 872,951

[22] Filed: Jan. 26, 1978

[51] Int. Cl.² .................. C07C 127/15; C07D 233/76
[52] U.S. Cl. ................................. 548/313; 260/553 R
[58] Field of Search .................... 548/313; 260/553 R, 260/583 K

[56] References Cited

U.S. PATENT DOCUMENTS 3,461,167  8/1969  Buehler et al. ................... 260/690 X
3,758,494  9/1973  Suverkropp et al. ................. 548/313
4,007,226  2/1977  Reynolds ..................... 260/583 K X
4,119,782  10/1978  Konijnenberg et al. ............. 548/313

FOREIGN PATENT DOCUMENTS 1180972  2/1970  United Kingdom ................ 260/583 K Primary Examiner—Richard Raymond
Attorney, Agent, or Firm—Cushman, Darby & Cushman

[57] ABSTRACT

An improved process for the preparation of 5-(4-aminobutyl)-hydantoin and/or 2-ureido-6-amino-hexanoic acid amide by the liquid phase hydrogenation of 5-(3-cyanopropyl)-hydantoin and/or 2-ureido-5-cyanopentanoic acid amide in the presence of ammonia, hydrogen and a hydrogenation catalyst. Catalyst dissolution into the reaction medium is reduced by utilizing a hydrogenation catalyst in a solid bed form and causing the compounds to be hydrogenated to pass through such solid bed catalyst.

7 Claims, No Drawings

PROCESS FOR THE PREPARATION OF 5-(4-AMINO BUTYL)-HYDANTOIN AND/OR 2-UREIDO-6-AMINO-HEXANOIC ACID AMIDE

The invention relates to the preparation of 5-(4-aminobutyl)-hydantoin and/or 2-ureido-6-amino-hexanoic acid amide by hydrogenation of 5-(3-cyanopropyl)-hydantoin and/or 2-ureido-5-cyano-pentanoic acid amide in the liquid phase in the presence of ammonia by means of a hydrogenation catalyst. A reaction product will then be obtained which can be converted into lysine by hydrolysis in a known way.

A hydrogenation process of this type can be effected with a high yield by means of various hydrogenation catalysts (see U.S. Pat. No. 3,758,494 and No. 3,911,001). But when the hydrogenation is effected in a suspension reactor with nickel and/or cobalt as the catalyst(s), it has been found that a not inconsiderable part of the catalyst, e.g. 1160 milligrams of nickel per liter of reaction liquid, may get lost by dissolution in the reaction medium.

It has now been found that the catalyst losses can be restricted by using the catalyst in the form of a solid bed and by passing the product to be hydrogenated over the catalyst in the liquid state.

The process according to the invention for the preparation of 5-(4-aminobutyl)-hydantoin and/or 2-ureido-6-amino hexanoic acid amide by hydrogenation of 5-(3-cyanopropyl)-hydantoin and/or 2-ureido-5-cyano-pentanoic acid amide in the liquid phase in the presence of ammonia by means of a hydrogenation catalyst is characterized in that the hydrogenation is effected with a catalyst in the form of a solid bed and the product to be hydrogenated is passed over the catalyst in the liquid state.

The process according to the invention may be effected at various temperatures, e.g. temperatures of 50°–250° C. Temperatures of 80°–160° C. are particularly suitable.

To change the product to be hydrogenated into the liquid state, various solvents may be used, such as, e.g., water, methanol, ethanol, isopropanol, butanols, glycols, dioxane, tetrahydrofuran, and other polar solvents or mixtures of polar solvents. The concentration of the product to be hydrogenated in the solvent may be varied, e.g., between 0.1 and 30% by weight. A concentration of 1–20% by weight is very satisfactory.

The partial hydrogen pressure may also be varied, e.g., between 1 and 500 atm. Partial hydrogen pressure of between 50 and 350 atmospheres are very suitable.

The catalyst used may be any of various hydrogenation catalysts known in the art. Use is preferably made of a hydrogenation catalyst containing cobalt, as the catalyst losses can then be reduced particularly well. The specific load of the catalyst may be varied, e.g., between 0.1 and 30 liters of liquid per liter of catalyst per hour. A specific load of between 0.5 and 15 liters of liquid per liter of catalyst per hour is very suitable.

The amount of ammonia used in the reaction mixture in the process according to the invention may vary. Use is normally made of a reaction mixture containing 10 to 30% by weight of ammonia.

The process according to the invention may be effected in various ways. A particularly suitable embodiment is the one in a so-called trickle-phase reactor. In this embodiment the product to be hydrogenated flows through the catalyst bed under the influence of gravity, while the hydrogen gas is passed through the catalyst bed as a counter-current or a parallel flow.

The invention will be elucidated further in the following examples.

EXAMPLE I

An aqueous solution containing 4.4% by weight of 5-(3-cyanopropyl)-hydantoin and 25% by weight of ammonia was pumped into the top of a vertically arranged metal tubular reactor (length 2.14 m, internal diameter 3.2 cm) at the rate of 2.5 liters per hour. The reactor contained 1.5 liters of catalyst. The catalyst used was a stabilized cobalt catalyst (83% by weight of cobalt, put on the market by Harshaw Chemical Company under the type reference Co-HP-037) in the form of small cylinders with a height of 4 mm and a diameter of 3 mm. The bulk density of the catalyst was 2190 grams per liter.

Along with the aqueous solution, hydrogen was fed to the top of the tubular reactor by means of a compressor at the rate of 2500 liters (0° C., 760 mm of Hg) per hour. The hydrogen pressure in the reactor was kept at 280 atmospheres. The temperature in the reactor was maintained at 110° C. by means of jacket heating.

The resulting reaction mixture was discharged from the bottom of the reactor, cooled with cooling water of 13° C., and separated into liquid and gas in a high-pressure separator.

After an operating time of 10 hours, a liquid sample was analysed by means of ion-exchange chromatography, which showed that no starting material was present anymore. A second sample was hydrolysed with hydrochloric acid, after which the amount of lysine then formed was also determined by means of ion-exchange chromatography. The determination showed a selectivity of 88%, (at least 88% of the cyano-hydantoin had been converted into hydrogenated product that could be hydrolysed to lysine). The cobalt content of the two liquid samples was 15 milligrams per liter.

EXAMPLE II

Example I was repeated, but with 1.7 liters of catalyst in the reactor and with a solution that also contained 0.6% by weight of 2-ureido-5-cyano-pentanoic acid amide and which was pumped in at the rate of 8 liters per hour. The conversion of the cyano starting product was 100% and the selectivity 89% (based on cyano-starting product).

The cobalt content of the cooled liquid reaction product was 38 mg/l.

EXAMPLE III

Example I was repeated, but with 1.7 liters of catalyst in the reactor, the solution being fed in at the rate of 1.4 liters per hour and the hydrogen being fed in at the rate of 1400 liters (N.T.P.) per hour. The catalyst used was nickel on kieselguhr (58% by weight of Ni, obtainable from Harshaw Chemical Company under the type reference Ni-0104) in the form of small cylinders with a diameter of 3 mm and a height of 4 mm. The bulk density was 1060 g/l.

The conversion was 100% and the selectivity 83%. The nickel content of the cooled liquid reaction product was 72 mg/l.

EXAMPLE IV

Example III was repeated, but at a hydrogen pressure of 150 atm. The conversion was 100% and the selectivity 82%. The nickel content of the liquid obtained was 130 mg/l.

EXAMPLE V

Example II was repeated, but with 1.1 liters of catalyst in the reactor.

The catalyst used was a mixture of Raney cobalt and graphite (5% by weight of graphite) in the form of tablets with a diameter of 3 mm. The feed rate of the solution was 4.4 liters per hour. The conversion was 89% and the selectivity 82%. The cobalt content of the resulting liquid amounted to 26 mg/l.

EXAMPLE VI

Example V was repeated, but at a reactor temperature of 140° C. The conversion was 96% and the selectivity 78%. The cobalt content of the liquid obtained was 21 mg/l.

We claim:

1. An improved process for the preparation of 5-(4-aminobutyl)-hydantoin by the hydrogenation of 5-(3-cyanopropyl)-hydantoin in a liquid phase in the presence of a hydrogenation catalyst, hydrogen and ammonia, said improvement consisting essentially of carrying out said hydrogenation in the presence of a hydrogenation catalyst in the form of a solid bed wherein said liquid phase containing 5-(3-cyanopropyl)-hydantoin is passed through said solid bed.

2. The process of claim 1 wherein said liquid phase is caused to pass through said solid bed of catalyst by the force of gravity.

3. The process of claim 1 wherein said liquid phase to be hydrogenated additionally contains 2-ureido-5-cyanopentanoic acid amide which is hydrogenated to 2-ureido-6-aminohexanoic acid amide.

4. The process of claim 1 wherein said catalyst contains a catalytically active component selected from the group consisting of cobalt, nickel and combinations thereof.

5. The process of claim 1 wherein said liquid phase to be hydrogenated essentially comprises 5-(3-cyanopropyl)-hydantoin in a polar solvent.

6. The process of claim 1 wherein the hydrogenation is carried out at a temperature of 80° to 160° C.

7. The process of claim 1 wherein the hydrogenation is carried out at a partial hydrogen pressure of 50 to 350 atmospheres.

* * * * *